United States Patent [19]

Nielsen et al.

[11] Patent Number: 5,288,627
[45] Date of Patent: Feb. 22, 1994

[54] **ENDOPROTEASE FROM *FUSARIUM OXYSPORUM* DSM 2672 FOR USE IN DETERGENTS**

[75] Inventors: Ruby I. Nielsen, Farum; Dorrit A. Aaslyng, Roskilde; Georg W. Jensen, Bagsvaerd; Palle Schneider, Ballerup, all of Denmark

[73] Assignee: Novo Nordisk A/S, Bagsvaerd, Denmark

[21] Appl. No.: 977,355

[22] Filed: Nov. 17, 1992

Related U.S. Application Data

[62] Division of Ser. No. 536,592, Jul. 3, 1990, abandoned.

[30] Foreign Application Priority Data

Jan. 7, 1988 [DK] Denmark .............................. 0062/88
Jan. 7, 1988 [DK] Denmark .............................. 0063/88

[51] Int. Cl.$^5$ .................... C12N 9/58; C12N 1/14; C12N 1/00; C11D 3/386
[52] U.S. Cl. .................... 435/223; 435/254.7; 435/929; 252/174.12; 252/DIG. 12
[58] Field of Search .................... 435/223, 254.7, 929; 252/174.12, DIG. 12

[56] References Cited

U.S. PATENT DOCUMENTS

| 3,652,399 | 3/1972 | Isono et al. ............... | 435/223 |
| 4,927,558 | 5/1990 | Aaslyng et al. ............ | 252/174.12 |
| 4,987,077 | 1/1991 | Charnley et al. ........... | 435/223 |

FOREIGN PATENT DOCUMENTS

WO88/07581 10/0988 PCT Int'l Appl.
WO88/03948 6/1988 PCT Int'l Appl.

OTHER PUBLICATIONS

Samal et al., Biotech. Bioengin., vol. 35, pp. 650–652 (1990).
Samal et al., Enzyme Microb. Technol., vol. 13, pp. 66–70 (1991).
Samal et al., Gene, vol. 85, pp. 329–333 (1989).
Samal et al., Molecular Microb., vol. 4, No. 10, pp. 1778–1792 (1990).
Tomoda et al., J. Takeda Res. Lab., vol. 38, No. 1/2, pp. 33–43 (1979).

*Primary Examiner*—David M. Naff
*Assistant Examiner*—Michael V. Meller
*Attorney, Agent, or Firm*—Steve T. Zelson; Elias J. Lambiris

[57] ABSTRACT

An endoprotease preparation, comprising an isolated endoprotease is disclosed. The endoprotease is a serine protease, shows immunochemical idenity to a protease derived from *Fusarium oxysporum* DSM 2672, hydrolyzes the oxidized beta-chain of bovine insulin at the peptide bonds Arg (22)-Gly (23) and Lys (29)-Ala(30), has optimum activity towards casein in the pH range of 8.5–11.0 with nearly constant activity in the pH range, has optimum activity at a temperature of about 45° C., and has an isolectric point of about 9.0–10.0. The preferred microorganism that the enzyme is isolated from is *Fusarium oxysporum* DSM 2672.

2 Claims, 14 Drawing Sheets

ENDOPROTEASE FROM *FUSARIUM OXYSPORUM* DSM 2672 FOR USE IN DETERGENTS

This is a divisional application of Ser. No. 07/536,592, filed Jul. 3, 1990, now abandoned.

TECHNICAL FIELD

This invention relates to a protease-containing detergent composition and to a proteolytic detergent additive for use therein.

BACKGROUND ART

Proteases are widely used as ingredients in commercial detergents to improve the detergency towards proteinaceous soiling. Further information on this may be found in the article "How Enzymes got into Detergents", vol. 12, Developments in Industrial Microbiology, a publication of the Society for Industrial Microbiology, American Institute of Biological Sciences, Washington, D.C. 1971, by Claus Dambmann, Poul Holm, Villy Jensen and Mogens Hilmer Nielsen, and in P.N. Christensen, K. Thomsen and S. Branner: "Development of Detergent Enzymes", paper presented on 9 October 1986 at the 2nd World Conference on Detergents held in Montreaux, Switzerland.

As indicated in said references, trypsin preparations were previously used in detergents, but since the 1960's alkaline *Bacillus* proteases have been used almost exclusively for this purpose, and in this period large efforts have been devoted to the development of microbial proteases with improved detergency. Detergents comprising alkaline *Bacillus* proteases are described e.g. in GB 1,342,784 and GB 1,356,130.

It is known that whereas pure trypsin is very specific hydrolyzing only a few peptide bonds in any given protein, the commonly used *Bacillus* proteases have a broad specificity and thus hydrolyze many bonds in a given substrate.

In the search for improved proteases it has been assumed that such a protease should have the broadest possible substrate specificity, i.e. it should be able to hydrolyze as many bonds as possible in the protein soiling.

Thus, M. Minagawa, Osaka Shiritsu Daigaku Seikatsu Kagaku-bu Kiyo, vol. 23, pp. 65-74 (1975) states on p. 68: "The type of protease adapted for use in the removal of protein stains must have a wide spectrum of substrate specificity capable of degrading the peptide bond, indiscriminately."

STATEMENT OF THE INVENTION

Surprisingly, we have now found that amino acid-specific proteases show excellent-detergency, and that the presence of non-specific proteases decrease the detergency.

We have thus observed an increasingly better performance when preparations containing mixtures of proteases are purified to contain only specific proteases. We have even observed purified specific proteases to be superior to the unspecific proteases used in detergents today.

Commercial preparations of the specific protease trypsin, which contain varying amounts of other proteases, have been used in detergents but the use of essentially pure trypsin in detergents is novel. Microbial specific proteases essentially free from other proteases are also known but their use in detergents is novel.

Our working hypothesis is that the improved detergency is due to the fact, that large peptide fragments are removed more efficiently during washing conditions. This may also explain why commercial preparations of trypsin, which contain varying amounts of other proteases have never been considered superior to the unspecific *Bacillus* proteases used in detergents today.

Accordingly, the first aspect of the invention provides a detergent composition comprising an endoprotease that hydrolyzes proteins by preferentially cleaving peptide bonds adjacent to one or two amino acids, characterized by being devoid of other proteases affecting detergency.

The second aspect of the invention provides a detergent additive comprising protease in the form of a non-dusting granulate, a stabilized liquid or a protected enzyme, characterized by comprising an endoprotease that hydrolyzes proteins by preferentially cleaving peptide bonds adjacent to one or two amino acids and by being devoid of other proteases affecting detergency.

DETAILED EXPLANATION OF THE INVENTION

Amino acid-specific protease

The class of proteases that may be used in the present invention are those endoproteases (endopeptidases) that hydrolyze proteins by preferentially cleaving peptide bonds adjacent to one or two amino acids giving rise to large peptide fragments. A number of such proteases are known, especially of animal and microbial origin. See K. Morihara: "*Comparative Specificity of Microbial Proteinases*", Adv. Enzymol. Relat. Areas Mol. Biol., 41, 179–243 (1974).

The specificity may be for bonds on the amino or carboxyl side of one or two specific amino acids. More particularly, the protease may have trypsin-like specificity, and it may be trypsin or microbial, trypsin-like protease.

The protease may be of serine, thiol, metal or aspartate type.

Recombinant DNA technology may be used to provide a microorganism containing a gene that encodes for and expresses and preferably also excretes the specific protease. This organism may be cultivated to produce protease for use in the invention.

Preferred specific proteases for use in the invention are active in the pH range 6–12, especially 7–10.5, and most preferably have pH optimum in either of these pH ranges.

The preparations of the invention are preferably essentially devoid of other proteases. Typically, specific protease (as defined above) makes up more than 90% and especially more than 95% of the total protease present, on weight basis or activity basis (e.g. measured in CPU, described below).

Usually, the specific protease activity will be provided essentially by a single specific protease. But a mixture of two (or more) specific proteases may be used, provided the mixture shows the stated specificity, e.g. a mixture of proteases with the same specificity.

One particularly preferred protease is a novel *Fusarium protease* discovered by the inventors and described below.

Novel Fusarium protease

The novel protease was isolated from a microbial strain which was deposited on 6 Jun. 1983 at Deutsche Sammlung von Mikroorganismen, Göttingen, West Germany under the terms of the Budapest Treaty the deposit No. DSM 2672. It was classified as belonging to *Fusarium oxysporum*.

Broth containing protease of the invention may be obtained by cultivating said strain according to principles known in the art, e.g. U.S. Pat. No. 3,652,399 (Takeda) or to an example of this specification.

The culture broth contains at least two proteases (I and II, with II being the protease of the invention) as well as other proteins. Separation can be made by affinity chromatography on a bacitracin-sepharose column, but it was found that a column of soy bean trypsin inhibitor-sepharose (STI-sepharose) has a better capacity.

By use of 0.05M boric acid, pH, 6.5 as buffer, proteases I and II will be bound, while the other proteins are eluted. The unwanted protease I can then be eluted by 0.25M NaCl in the same buffer, by 0.1M NaCl or by 0.05M boric acid at pH 4-5 or below. Protease II (protease of the invention) can finally be eluted by 0.05M acetic acid, pH 2.8.

SDS-PAGE and isoelectric focusing (IEF) in the presence of marker proteins are convenient methods for molecular weight (MW) and isoelectric point (pI) determinations, respectively. According to these methods, protease of the invention has MW of about 27 kD and pI of 9-10. Protease I (described above) has MW of about 30 kD and pI 9-10, and prior-art *Fusarium* protease produced by cultivation of strain S-19-5 according to U.S. Pat. No. 3,652,399 contains a single component with MW of about 32 kD by the above method.

The pH and temperature dependence of activity are shown in FIGS. 2 and 3, where protease I is also shown for comparison. The curves are based on the CPU method (described below), except that temperature or pH is varied. As shown in the figures, protease of the invention has temperature optimum around 45° C. (30 minutes reaction at pH 9.5), and pH optimum at 8.5-11.0 (30 minutes reaction at 25° C.) with nearly constant activity in that pH range.

The pH and temperature curves were also measured in solutions of a built liquid detergent and of a powder detergent with perborate and TAED (bleach activator). These curves were nearly identical to those without detergent shown in FIGS. 2 and 3.

The protease is inhibited by inhibitors characteristic for serine proteases, such as PMSF.

To illustrate the specificity, oxidized B-chain of bovine insulin was hydrolyzed by protease (1.38 CPU/l, 15 min), and the hydrolysis products were analyzed by reverse-phase liquid chromatography (5 micron silica coated with C-18 hydrocarbon, gradient elution). FIG. 4 shows the results with protease of the invention, FIG. 5 with component I from DSM 2672, and FIGS. 6-7 with prior-art *Fusarium proteases* according to U.S. Pat. No. 3,652,399 (*Fusarium sp.* S-19-5 and *F. oxysporum f. batatas* IFO 4468, respectively).

The chromatograms show a striking difference. That of the protease of the invention has only two major peaks and appears to be similar to the chromatogram obtained with trypsin, which is known to hydrolyze two peptide bonds (Arg(22)-Gly(23) and Lys(29)-Ala(30)). In contrast, the other *Fusarium proteases* hydrolyze a multitude of bonds in this substrate, resulting in more than 10 peaks of comparable size.

The substrate specificity is also illustrated by the action on two synthetic substrates. Protease of the invention hydrolyzes Bz-Arg-pNA but not Suc-AAPF-pNA. Protease I, in contrast, hydrolyzes only the latter.

Monospecific antisera against purified protease may be raised for example by immunizing rabbits according to the regimen described by N. Axelsen et al. in: A manual of Quantitative Immunoelectrophoresis, Blackwell Scientific Publications, 1973, chapter 23. Purified immunoglobulins may be obtained from the antisera, for example by salt precipitation ($(NH_4)_2SO_4$), followed by dialysis and ion exchange chromatography, e.g. on DEAE-Sephadex.

Immunochemical characterization of proteins may be conducted either by Ouchterlony double-diffusion analysis (O. Ouchterlony in: Handbook of Experimental Immunology (D.M. Weir, Ed.), Blackwell Scientific Publications, 1967, pp. 655-706), by crossed immunoelectrophoresis (N. Axelsen et al., supra, chapters 3 and 4), or by rocket immunoelectrophoresis (N. Axelsen et al., supra, Chapter 2).

The protease of the invention shows immunochemical non-identity to protease I from DSM 2672 and to S-19-5 prior-art *Fusarium protease*.

Detergent composition

The detergent compositions of the invention comprise surfactant which may be of the anionic, non-ionic, cationic, amphoteric or zwitterionic type, or a mixture of these. Typical examples of anionic surfactant are linear alkyl benzene sulfonate (LAS), alpha olefin sulfonate (AOS), alcohol ethoxy sulfate (AES) and natural soap of alkali metals.

The detergent according to the invention may contain other detergent ingredients known in the art, such as builders, bleaching agents, bleach activators, anti-corrosion agents, sequestering agents, anti-soil redeposition agents, perfumes, stabilizers for the enzymes and bleaching agents and so on.

The detergent compositions of the invention can be formulated in any convenient form, such as powders, liquids, etc. The protease may be stabilized in a liquid detergent by inclusion of enzyme stabilizers, e.g. those mentioned above.

Detergents usually have a pH in solution of 7-12, especially 8-10.5. Specific protease with activity at this pH is preferred.

The detergent of the invention may contain one or more other detergent enzymes in addition to protease of the invention. Examples are lipase, amylase and cellulase. It is known that when combining a protease with another enzyme in a detergent, the other enzyme becomes liable to digestion and deactivation by the protease in the detergent solution (see e.g. EP 205,208 (Unilever). In this connection, the high substrate specificity of the protease of the invention makes it more compatible with other enzymes. The two (or more) enzymes may be added separately or in the form of a combined additive.

Detergent additive

The detergent additive of the invention is in the form of a non-dusting granulate, a stabilized liquid or a protected enzyme.

Non-dusting granulates may be produced e.g. according to NL 167,993 (Novo), U.S. Pat. No. 4,106,991

(Novo) or U.S. Pat. No. 4,661,452 (Novo) and may optionally be coated according to principles known in the art.

A liquid protease preparation may be stabilized e.g. by adding propylene glycol, other polyols, sugars, sugar alcohols, lactic acid, boric acid. Other enzyme stabilizers are known in the art.

A protected enzyme may be produced according to EP 238,216 (Novo, Albright & Wilson).

The detergent additive of the invention may contain one or more other detergent enzymes, e.g. lipase, cellulase or amylase. In the case of a granulate, the enzymes may be mixed before or after granulation.

Protease activity (CPU)

Proteolytic activity is determined with casein as the substrate. One Casein Protease Unit (CPU) is defined as the amount of enzyme liberating 1 millimole of primary amino groups (determined by comparison with a serine standard) per minute under standard conditions, i.e. incubation for 30 minutes at 25° C. and pH 9.5.

A 2% (w/v) solution of casein (Hammarsten, supplied by Merck A.G., West Germany) is prepared with the Universal Buffer described by Britton and Robinson (Journ.Chem.Soc. 1931, p. 1451), adjusted to pH 9.5.

Two ml of substrate solution is preincubated in a water bath for 10 minutes at 25° C. 1 ml of enzyme solution containing b g/ml of enzyme preparation, corresponding to about 0.2–0.3 CPU/ml of Britton-Robinson buffer (pH 9.5), is added. After 30 minutes of incubation at 25° C. the reaction is terminated by the addition of a stopping agent (5 ml of a solution containing trichloroacetic acid (17.9 g), sodium acetate (29.9 g), and acetic acid (19.8 g), filled up to 500 ml with deionized water). A blank is prepared in the same manner as the test solution, except that the stopping agent is added prior to the enzyme solution.

The reaction mixtures are kept for 20 minutes in the water bath, whereupon they are filtered through Whatman ® 42 paper filters.

Primary amino groups are determined by their color development with o-phthaldialdehyde (OPA).

Disodium tetraborate decahydrate (7.62 g) and sodium dodecylsulfate (2.0 g) is dissolved in 150 ml of water. OPA (160 mg) dissolved in 4 ml of methanol is then added together with 400 μl of beta-mercaptoethanol, whereafter the solution is made up to 200 ml with water.

To the OPA reagent (3 ml) is added 400 μl of the above-mentioned filtrates with mixing. The optical density (OD) at 340 nm is measured after about 5 minutes.

The OPA test is also performed with a serine standard containing 10 mg of serine in 100 ml of Britton-Robinson buffer (pH 9.5). The buffer is used as a blank.

The protease activity is calculated from the optical density measurements by means of the following formula:

$$CPU/ml \text{ of enzyme solution} = \frac{(OD_t - OD_b) \times C_{ser} \times Q}{(OD_{ser} - OD_B) \times MW_{ser} \times t_i}$$

$CPU/g$ of enzyme preparation $= CPU/ml$: $b$ wherein $OD_t$, $OD_b$, $OD_{ser}$ and $OD_B$ is the optical density of the test solution, blank, serine standard, and buffer, respectively, $C_{ser}$ the concentration of serine in mg/ml in the standard, $MW_{ser}$ the molecular weight of serine. Q is the dilution factor (in this instance equal to 8) for the enzyme solution, and $t_i$ is the incubation time in minutes.

BRIEF DESCRIPTION OF THE DRAWINGS

FIG. 4 shows hydrolysis with protease of the invention, FIG. 5 with protease I from DSM 2672, FIG. 6 with protease from S-19-5, and FIG. 7 with protease from *F. oxysporum f. batatas* (IFO 4468), the two latter prepared according to U.S. Pat. No. 3,652,399.

EXAMPLES

EXAMPLE 1

*Fermentation of F. oxysporum DSM 2672*

A seed fermenter with the below medium was inoculated with DSM 2672 and fermented for 30–35 hours with aeration. It was then used for seeding a 10 times larger main fermenter with the same medium and fermented for 114 hours with aeration and with continuous dosing of additional substrate.

Medium composition (w/v %):

| | |
|---|---|
| Soy meal | 5.0 |
| glucose | 5.0 |
| $KH_2PO_4$ | 2.0 |
| $K_2HPO_4$ | 2.0 |
| $CaCl_2.2H_2O$ | 0.02 |
| $MgSO_4.7H_2O$ | 0.02 |
| Soy bean oil | 0.5 |
| Pluronic ® (ml/l) | 0.033 |

Substrate dosed: 45% w/v glucose
dosing rate: 0.28% vol/vol/hour

The protease activity of the broth was 2.84 AU/l (AU indicates protease activity in Anson Units, see U.S. Pat. No. 3,723,250, col. 8).

Crude protease was recovered from the culture broth by addition of ammonium sulfate (salting out), filtration, redissolution of filter cake, purification by ion exhange followed by bentonite, and finally drying.

EXAMPLE 2

Separation of proteases

Crude protease obtained as in Example 1 (activity 15 CPU/g) was dissolved in buffer (0.05M boric acid, pH 6.5). After decolorization by adsorption on DEAE-Sephadex, the OD was 1.2 at 280 nm. 15 ml of this solution with a total protein content of 18 mg (calculated from OD, 280 nm), was separated by affinity chromatography.

Figure 1:
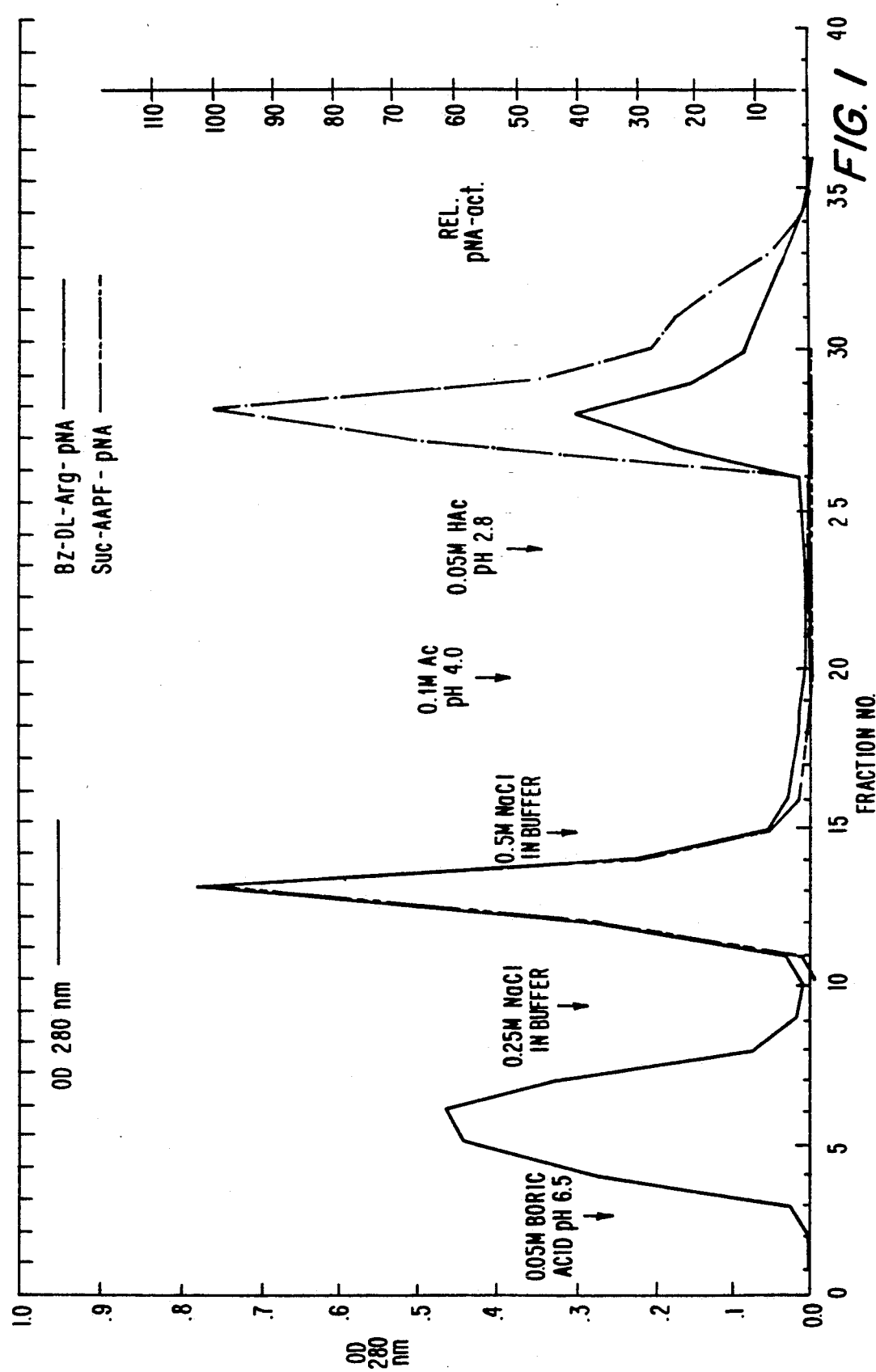
FIG. 1 shows the elution chromatogram of culture broth from strain DSM 2672 on a STI-Sepharose column. Details are given in Example 2.
Figure 2:
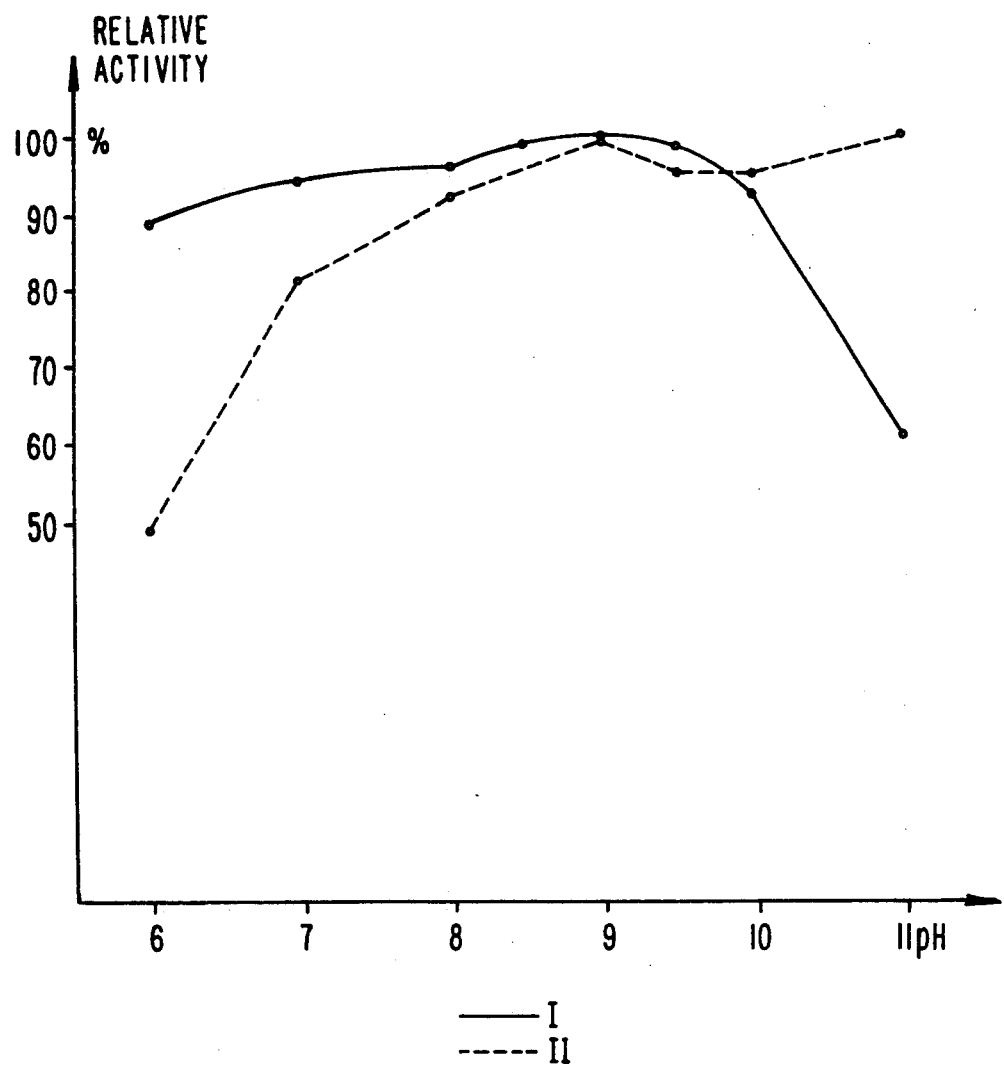
FIGS. 2 and 3 show the pH-activity and temperature activity curves, respectively, of the two proteases from DSM 2672, viz. protease II (protease of the invention) and protease I for comparison.
Figure 3:
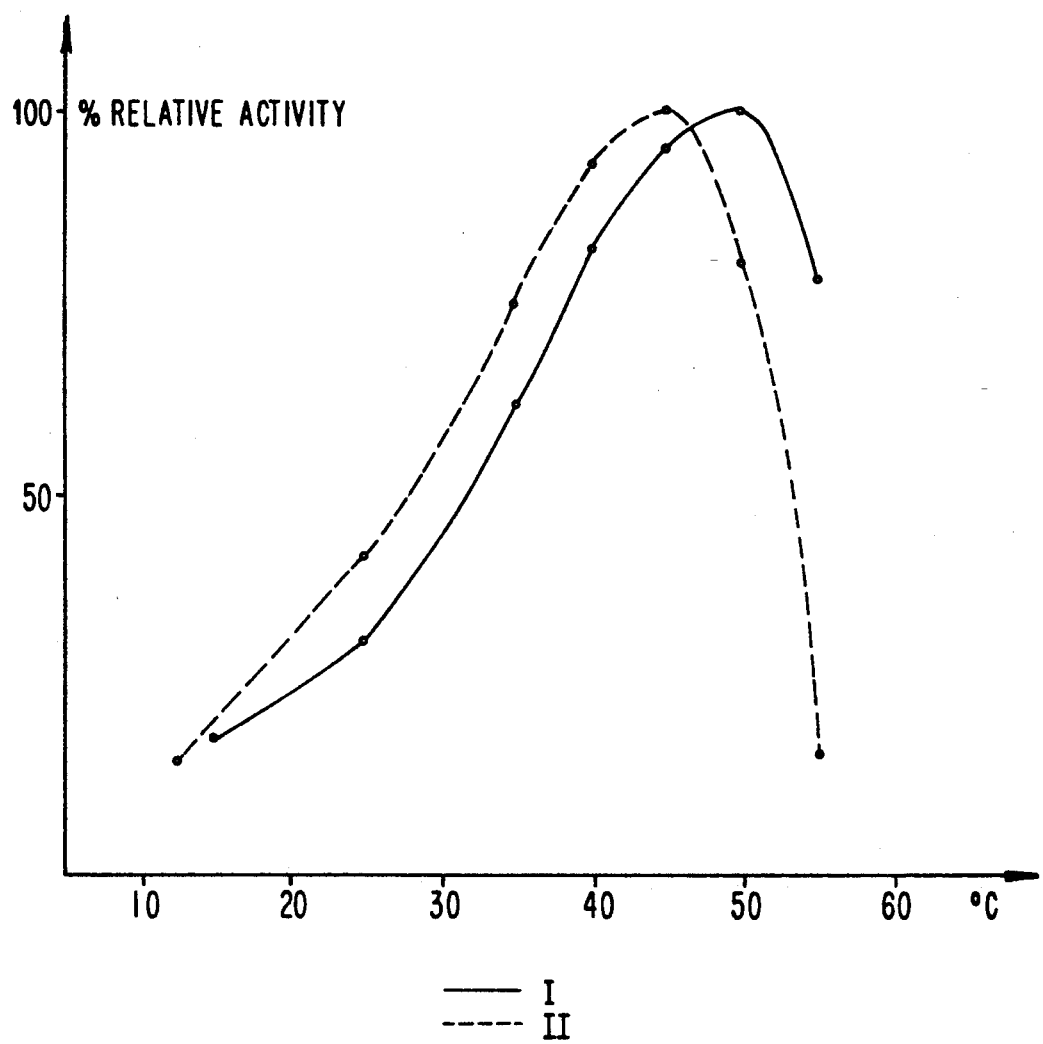
Figure 4:
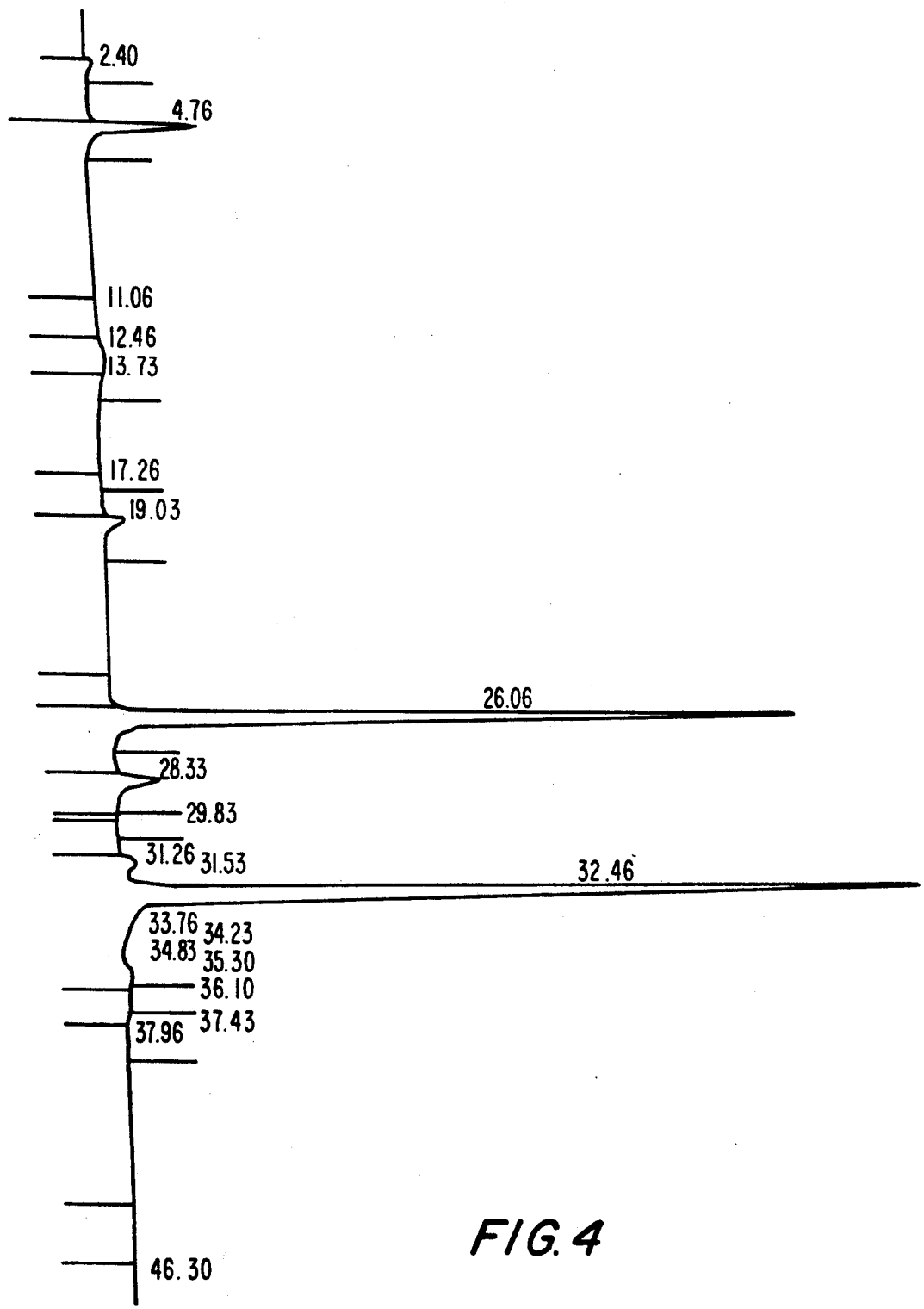
FIGS. 4 –7 show reverse-phase chromatograms of hydrolysis products of oxidized B-chain of bovine insulin with *Fusarium proteases*.
Figure 5:
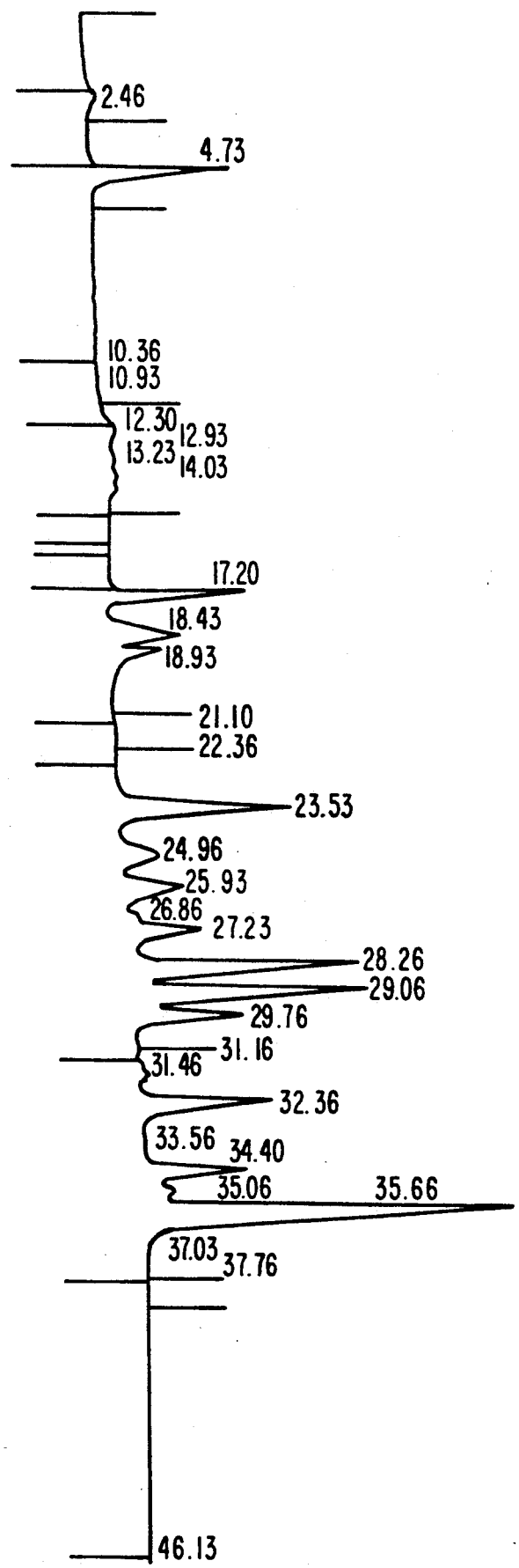
Figure 6:
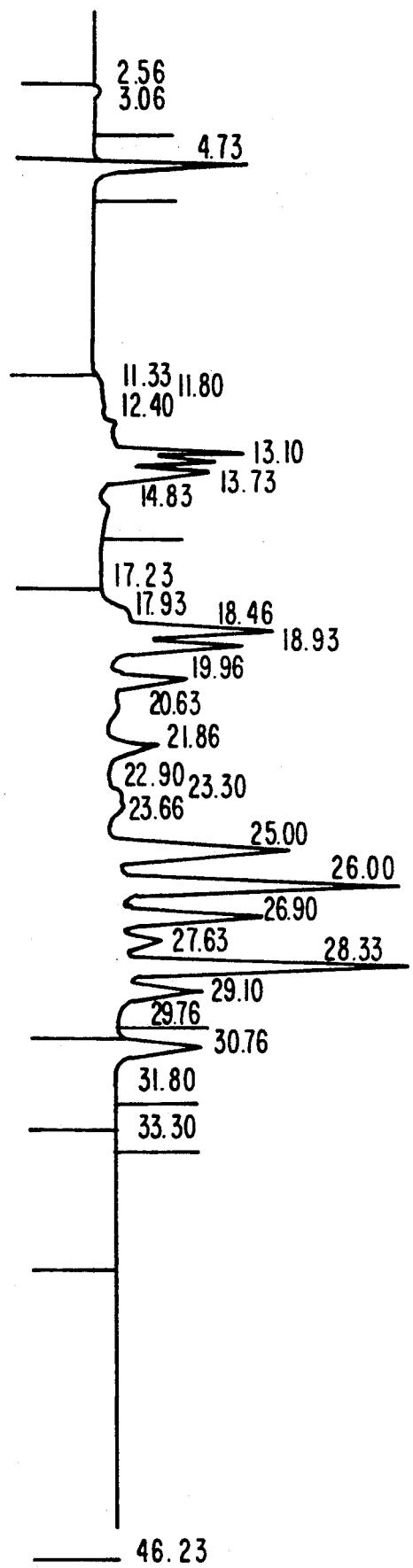
Figure 7:
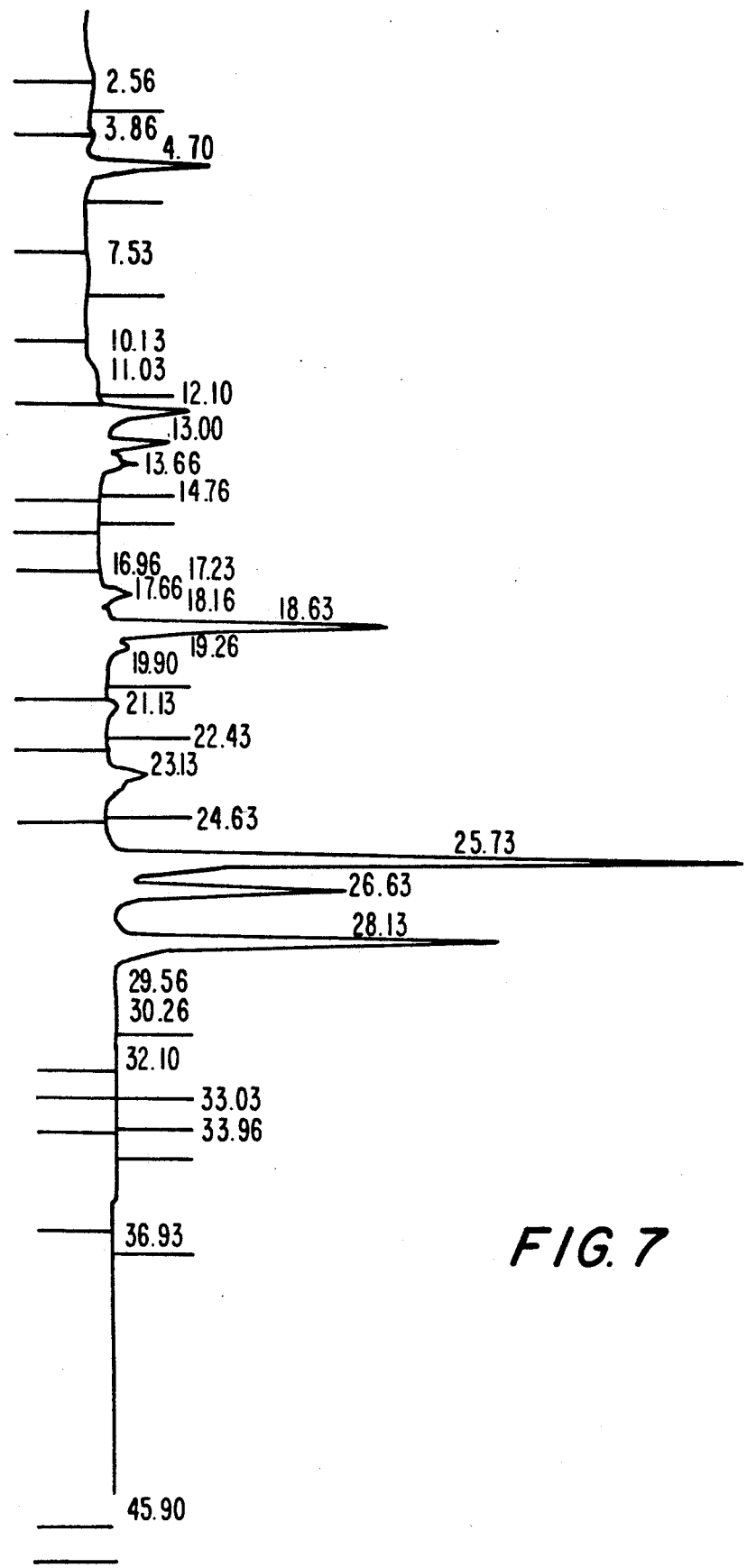

The gel was soy bean trypsin inhibitor-agarose (STI-agarose), the bed volume was 10 ml, and the column diameter was 2.5 cm. The above buffer was used, with a flow rate of 0.5 ml/min, and fractions of 4.5 ml each were collected. For each fraction, OD 280 nm was measured, as well as activity towards Bz-DL-Arg-pNA and Suc-AAPF-pNA. The elution chromatogram is shown in FIG. 1. The eluent used at each stage is also indicated in the figure.

As shown in FIG. 1, unadsorbed material was first eluted with buffer, then a protease peak (termed I) was eluted by 0.25M NaCl in buffer. As shown, increase to 0.5M NaCl and application of 0.1M acetate, pH 4.0 eluted no further material. A second protease peak (termed II) was eluted by 0.05M acetic acid, pH 2.8.

Distribution of protein:

| Distribution of protein: | |
|---|---|
| Injected Eluted | 18 mg |
| Not adsorbed | 7.45 mg (41%) |
| Component I | 6.55 mg (36%) |
| Component II | 4.03 mg (22%) |
| Total | 18 mg |

Approx. 64% of the protein remained in solution after the initial purification by DEAE, so the protein recovery in relation to the protease concentrate was as follows:

| Component I | 23% of protein (62% of protease) |
|---|---|
| Component II | 14% of protein (38% of protease) |

EXAMPLES 3-8

Washing trials

The following detergent solutions (in g/l) were used. Nos. I-III represent powder detergents, and No. IV a liquid built detergent.

| | I | II | III |
|---|---|---|---|
| LAS | 0.4 | 0.4 | 0.4 |
| AE | 0.15 | 0.15 | 0.15 |
| Soap | 0.15 | 0.15 | 0.15 |
| Sodium tripolyphosphate | 1.75 | — | 1.75 |
| Sodium silicate | 0.4 | 0.4 | 0.4 |
| Carboxy methyl cellulose | 0.05 | 0.05 | 0.05 |
| EDTA | 0.01 | 0.01 | 0.01 |
| Sodium sulfate | 2.1 | 2.1 | 2.1 |
| Sodium perborate | — | — | 1.0 |
| TAED | — | — | 0.1 |
| Zeolite A | — | 1.25 | — |
| NTA | — | 0.5 | — |
| Sodium carbonate | — | 0.5 | — |
| NaOH to pH: | 9.5 | 10.0 | 9.5 |

| | IV |
|---|---|
| AES | 0.23 |
| AE | 0.23 |
| Oleic acid | 0.075 |
| Triethanolamine | 0.15 |
| Ethanol | 0.03 |
| Propylene glycol | 0.15 |
| DTPA | 0.008 |
| Disodium citrate, 2H$_2$O | 0.17 |
| CaCl$_2$, 2H$_2$O | 0.015 |
| NaOH to pH: | 8.0 |

LAS is linear alkyl benzene sulfonate (Nansa 80S, product of Albright & Wilson, UK), AE is alcohol ethoxylate (Berol 065, product of Berol Kemi AB, Sweden), EDTA is ethylene diamine tetra-acetic acid, TAED is N,N,N,N-tetra-acetyl ethylene diamine, NTA is nitrilotriacetic acid, AES is alcohol ethoxy sulfate (Dobanol 25-3S, product of Shell Chemicals), DTPA is diethylene triamine penta-acetic acid tri-sodium monocalcium salt.

Soiled spinach swatches were made on a Mathis Washing and Drying Unit (Werner Mathis AG, Switzerland) in continuous operation, whereby cotton textile passes through spinach juice, is squeezed between two rollers and is then blown dried with 30° C. air (thermostated). The swatches were aged for 3 weeks at 20° C., and were then kept at −18° C. until use.

Swatches with mixed soiling were made by immersing cotton in the below mixture; squeezing between rollers; drying and aging for 2 days in air at 20° C.

| Olive oil | 14.4 | weight | % |
|---|---|---|---|
| Stearic acid | 1.8 | — | — |
| Monoglyceride | 1.8 | — | — |
| Gelatine | 0.9 | — | — |
| Deionized water | 79.3 | — | — |
| Carbon black | 0.2 | — | — |
| China clay | 1.4 | — | — |
| Indian ink | 0.2 | — | — |

Washing tests were made in a Terg-O-Tometer (Jay C. Harris: Detergency Evaluation and Testing, Interscience Publishers Ltd. (1954), pp. 60-61) with 7 swatches (7×7 cm) and 700 ml detergent solution in each beaker. Conditions were 25° C., 10 min, 100 rpm. After rinsing and drying, reflectance (R) of the swatches at 460 nm was measured. The washing performance is expressed as delta $R = R - R_o$, where $R_o$ is the measurement without enzyme.

Protease of the invention (prepared as in Example 2) was compared to component I (prepared as in Example 2) and to Savinase ® (an alkaline *Bacillus protease*, product of Novo Industri A/S, Denmark).

Figure 8:
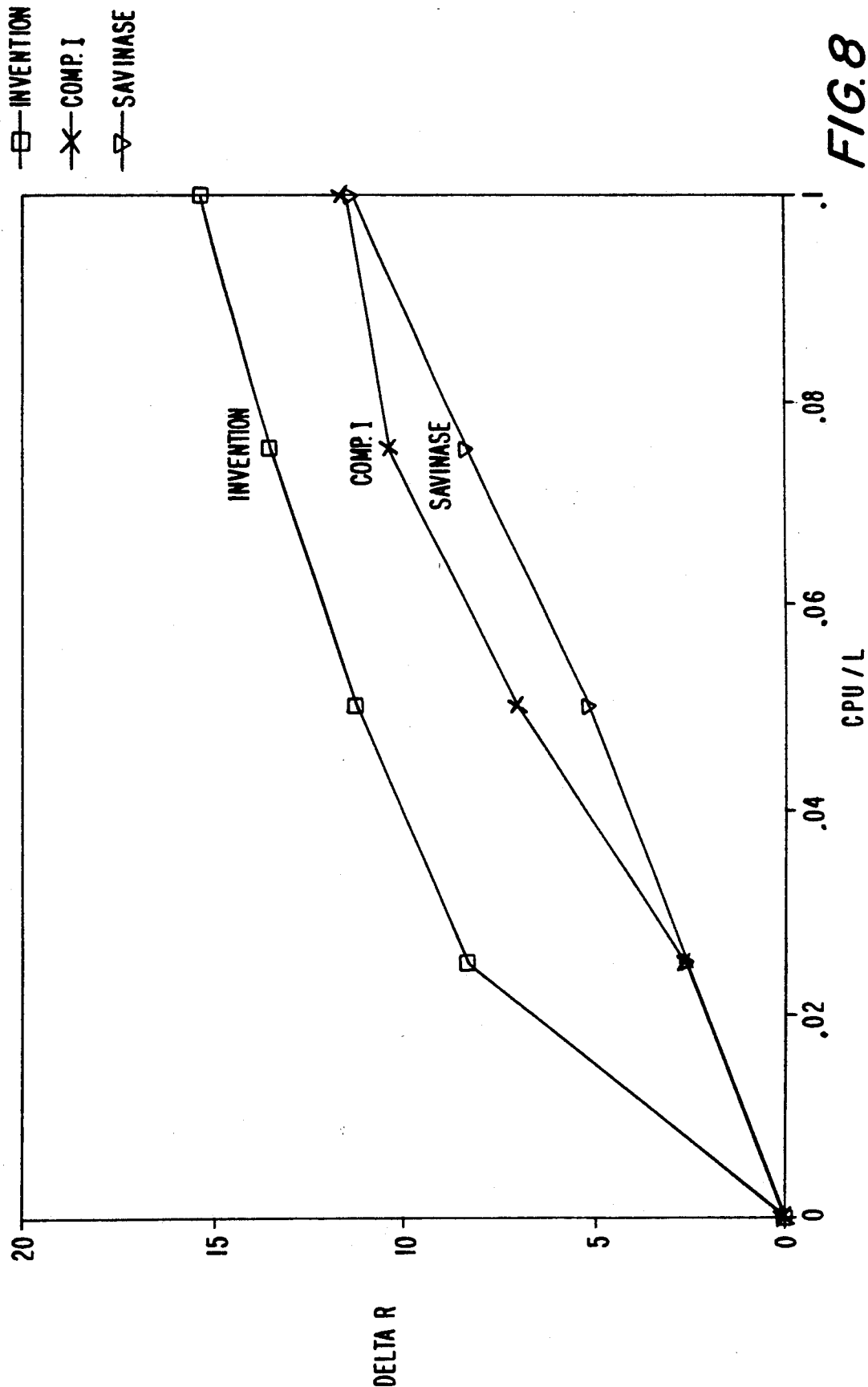
FIGS. 8–13 show the results of the washing trials of Examples 3–8, respectively.

Results are given as $R_o$ and delta R versus protease type and dosage (in CPU/l). The results are also shown below in the figures as indicated:

Example 3 (FIG. 8)

| | Det. I, spinach soiling | | | | |
|---|---|---|---|---|---|
| | | CPU/l | | | |
| | 0 | 0.025 | 0.05 | 0.075 | 0.1 |
| Protease | $R_o$ | delta R | delta R | delta R | delta R |
| Invention | | 8.3 | 11.2 | 13.5 | 15.3 |
| Comp. I | 42.2 | 2.6 | 7.0 | 10.3 | 11.5 |
| Savinase | | 2.5 | 5.1 | 8.3 | 11.3 |

Figure 9:
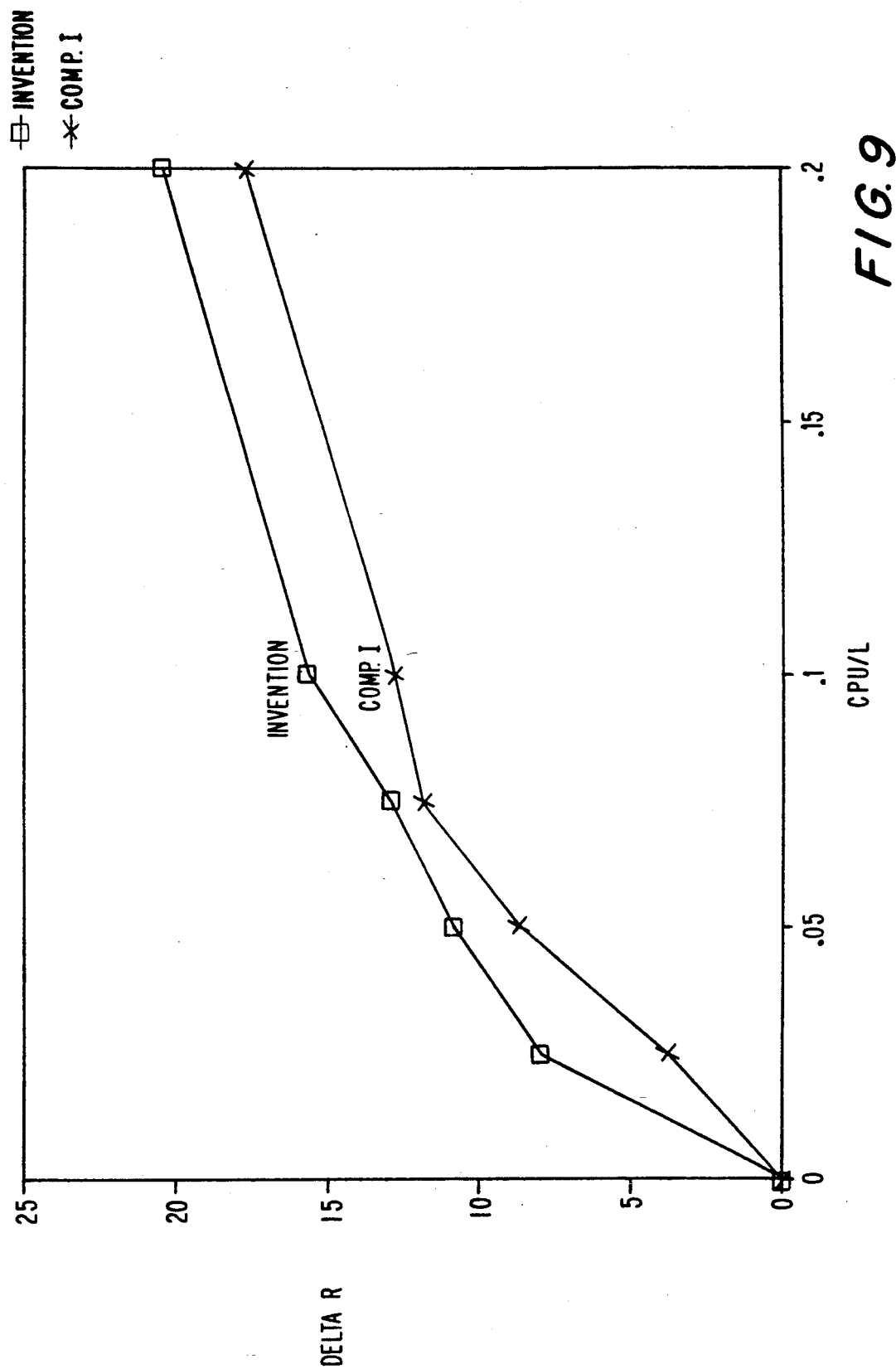

Example 4 (FIG. 9)

| | Det. II, spinach soiling | | | | | |
|---|---|---|---|---|---|---|
| | | CPU/l | | | | |
| | 0 | 0.025 | 0.05 | 0.075 | 0.1 | 0.2 |
| Protease | $R_o$ | delta R | delta R | delta R | delta R | delta R |
| Invention | | 7.9 | 10.7 | 12.8 | 15.5 | 20.3 |
| Comp. I | 43.4 | 3.7 | 8.6 | 11.7 | 12.6 | 17.6 |

Figure 10:
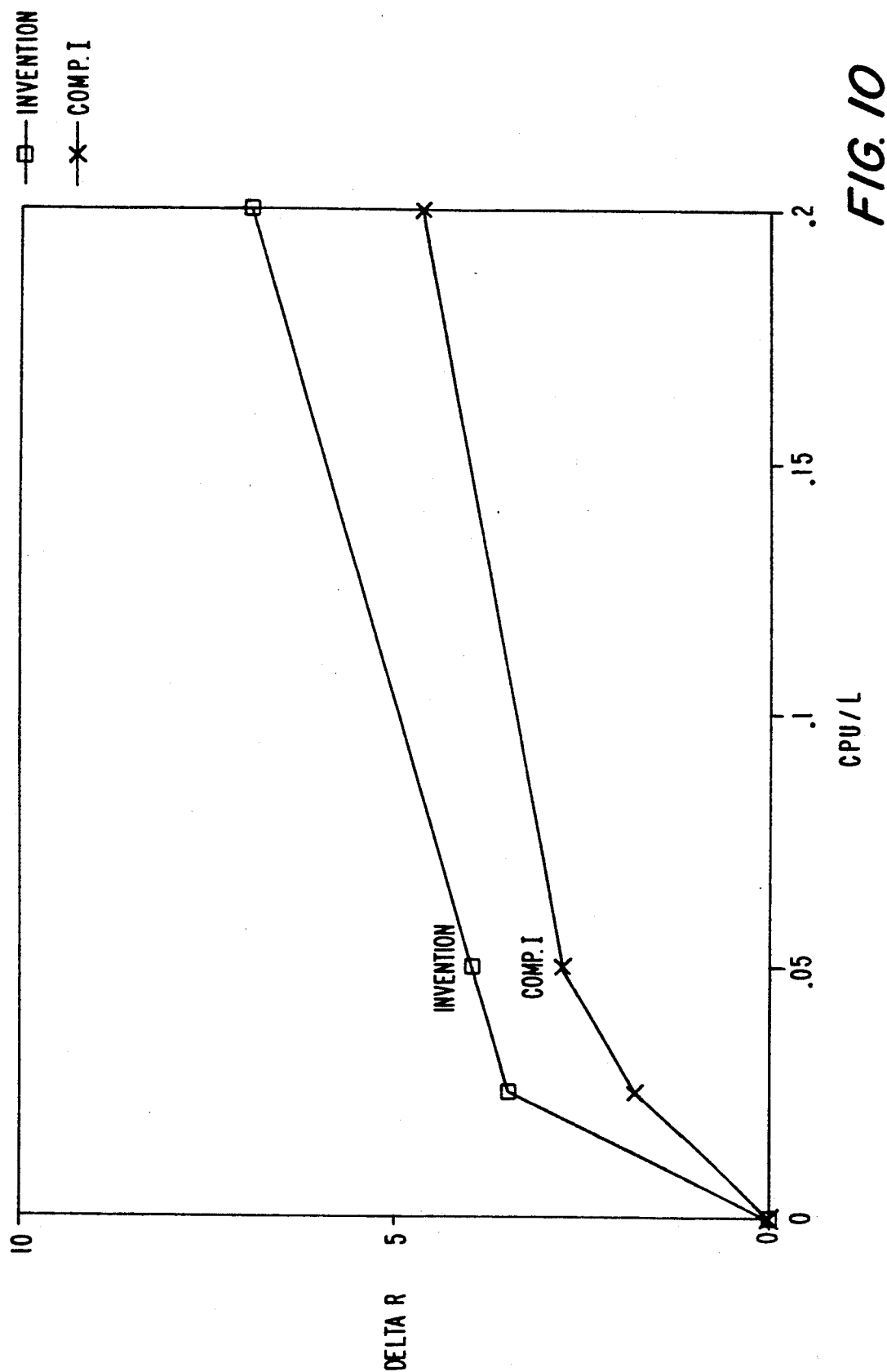

Example 5 (FIG. 10)

| | Det. IV, spinach soiling | | | |
| --- | --- | --- | --- | --- |
| | | CPU/l | | |
| Protease | 0<br>$R_o$ | 0.025<br>delta R | 0.05<br>delta R | 0.2<br>delta R |
| Invention | | 3.5 | 4.0 | 7.0 |
| Comp. I | 37.7 | 1.8 | 2.8 | 4.7 |

Figure 11:
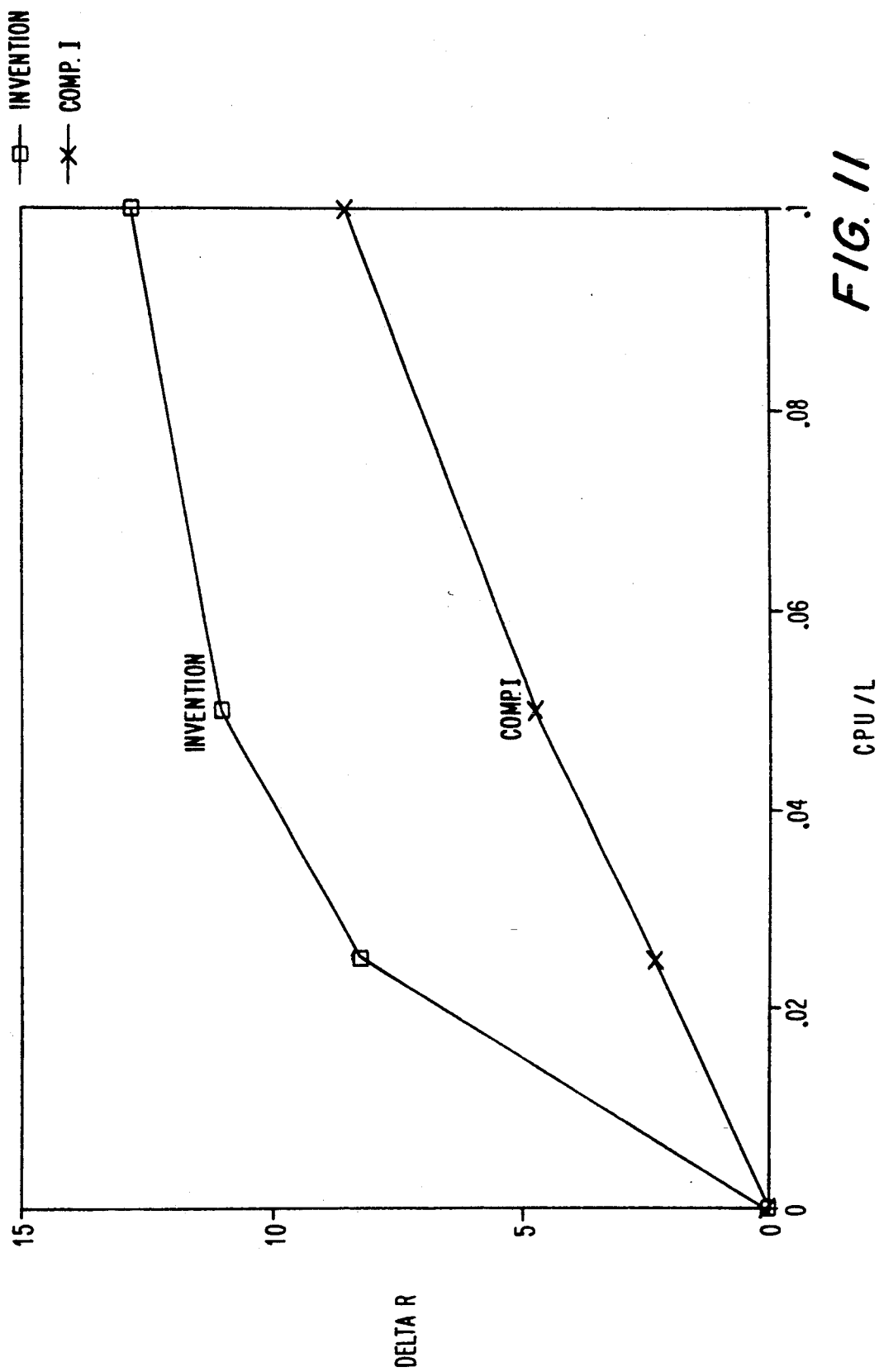

Example 6 (FIG. 11)

| | Det. I, mixed soiling | | | |
| --- | --- | --- | --- | --- |
| | | CPU/l | | |
| Protease | 0<br>$R_o$ | 0.025<br>delta R | 0.05<br>delta R | 0.1<br>delta R |
| Invention | | 8.2 | 11.0 | 12.8 |
| Comp. I | 21.0 | 2.3 | 4.7 | 8.5 |

Figure 12:
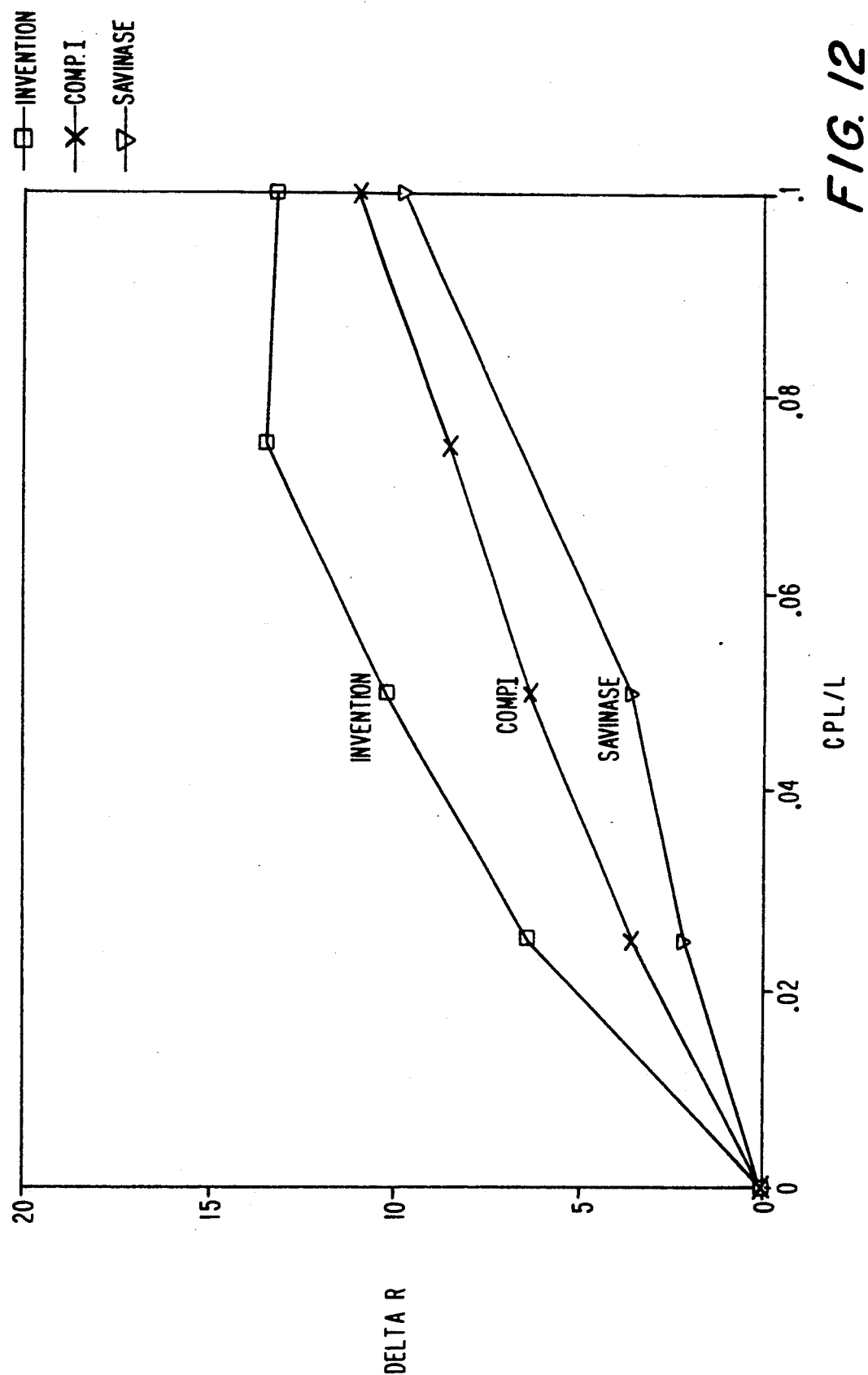

Example 7 (FIG. 12)

| | Det. III, spinach soiling | | | | |
| --- | --- | --- | --- | --- | --- |
| | | CPU/l | | | |
| Protease | 0<br>$R_o$ | 0.025<br>delta R | 0.05<br>delta R | 0.075<br>delta R | 0.1<br>delta R |
| Invention | | 6.4 | 10.2 | 13.5 | 13.2 |
| Comp. I | 40.5 | 3.6 | 6.4 | 8.5 | 10.9 |
| Savinase | | 2.2 | 3.6 | | 9.7 |

Figure 13:
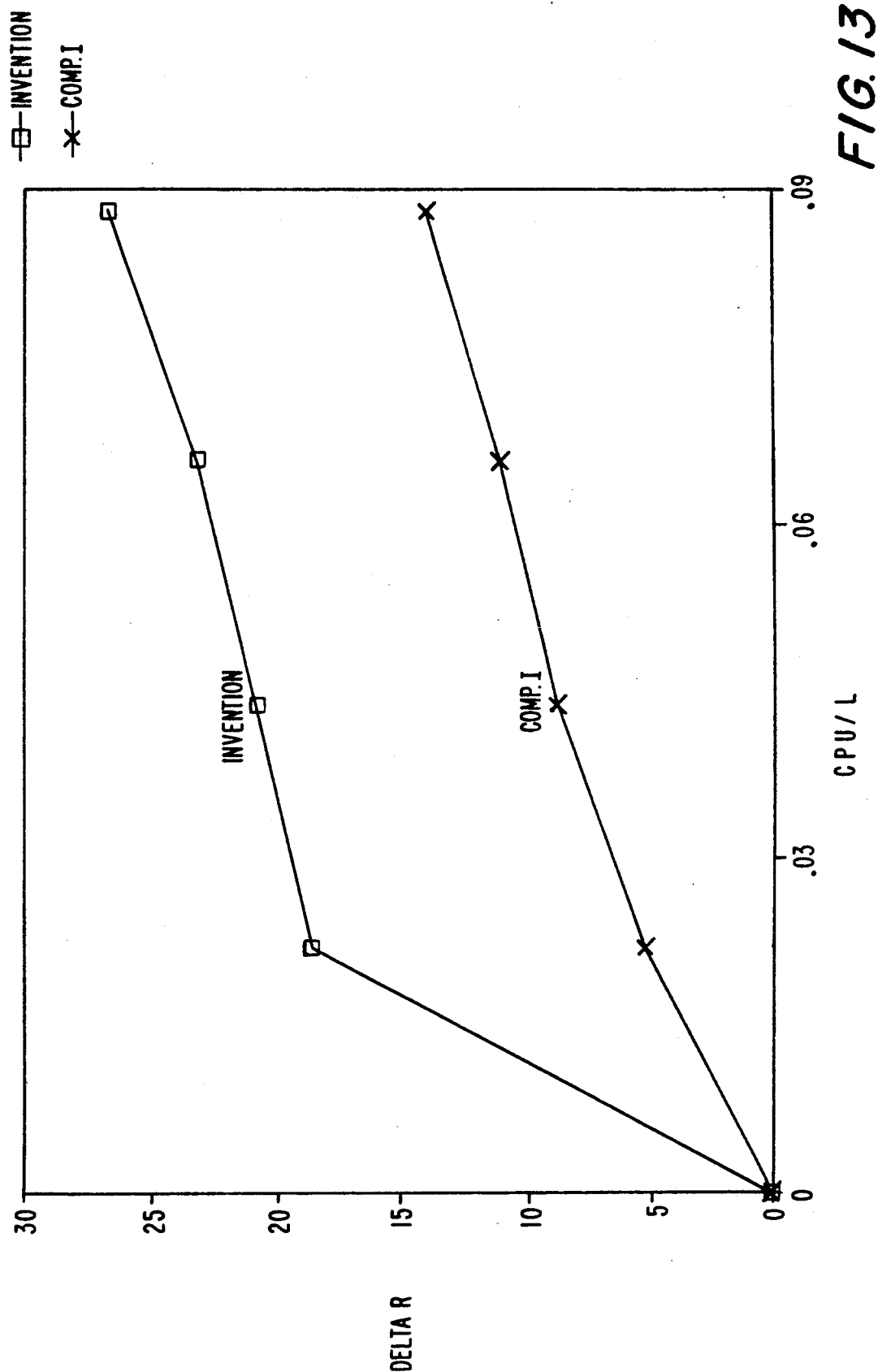

Example 8 (FIG. 13)

| | Det. II, mixed soiling | | | | |
| --- | --- | --- | --- | --- | --- |
| | | CPU/l | | | |
| Protease | 0<br>$R_o$ | 0.022<br>delta R | 0.044<br>delta R | 0.066<br>delta R | 0.088<br>delta R |
| Invention | | 18.5 | 20.7 | 23.1 | 26.6 |
| Comp. I | 21.5 | 5.2 | 8.8 | 11.0 | 13.9 |

The detergent formulations tested cover pH 8–10, with various builders (phosphate and non-phosphate) with and without perborate, and with anionic and nonionic surfactant. Thus, a wide range of typical formulations for liquid and powder detergents have been covered. At all these conditions, protease of the invention showed superior washing effect on the basis of CPU activity.

EXAMPLE 9

Washing trials with protease mixtures

Detergent No. I of examples 3–8 was used. Swatches and washing conditions were as in examples 3–8. The protease of the invention, component I and various mixtures of these were added at total dosage up to 0.10 CPU/l.

| Protease<br>ratio | | CPU/l | | |
| --- | --- | --- | --- | --- |
| Invention<br>:comp. I | 0<br>$R_o$ | 0.01<br>delta R | 0.05<br>delta R | 0.10<br>delta R |
| 0:100 | 45.1 | 1.8 | 7.1 | 9.7 |
| 50:50 | 44.7 | 1.7 | 9.1 | 11.5 |
| 75:25 | 44.7 | 2.1 | 8.8 | 11.2 |
| 90:10 | 45.1 | 2.0 | 9.1 | 11.2 |
| 99:1 | 45.1 | 2.2 | 9.5 | 12.2 |
| 100:0 | 44.7 | 2.2 | 11.0 | 14.3 |

It is seen that increasing purity of the specific protease gives increased washing performance.

EXAMPLE 10

Washing trial with Asp-N specific protease

The following detergent formulation was used:

| LAS | 0.40 g/l |
| --- | --- |
| AE | 0.15 g/l |
| Soap | 0.15 g/l |
| $Na_2SO_4$ | 2.00 g/l |

The same chemicals as described in examples 3–8 were used.

The detergent was dissolved in 10 mM $NH_4HCO_3$ prepared from 9° GH water, and pH was adjusted to 8.0.

Soiled spinach swatches were prepared like in examples 3–8.

Washing tests were made in 150 ml glass beakers in a thermostat water bath with magnetic stirring with 6 swatches (2.2×2.2 cm each) and 60 ml detergent solution in each beaker. Conditions were 35° C., 90 min.

As another example of specific proteases, the specific protease Asp-N endoproteinase commercially available from Boehringer (cat. No. 1054 589) is compared to the unspecific Alcalase ® and Subtilisin Novo (both *Bacillus proteases*, products of Novo Industri A/S, Denmark).

The proteases are dosed on equal amounts of enzyme protein, 0.6 and 1.2 mg/l.

After rinsing and drying, reflectance (% R) of the swatches was measured according to examples 3–8.

Figure 14:
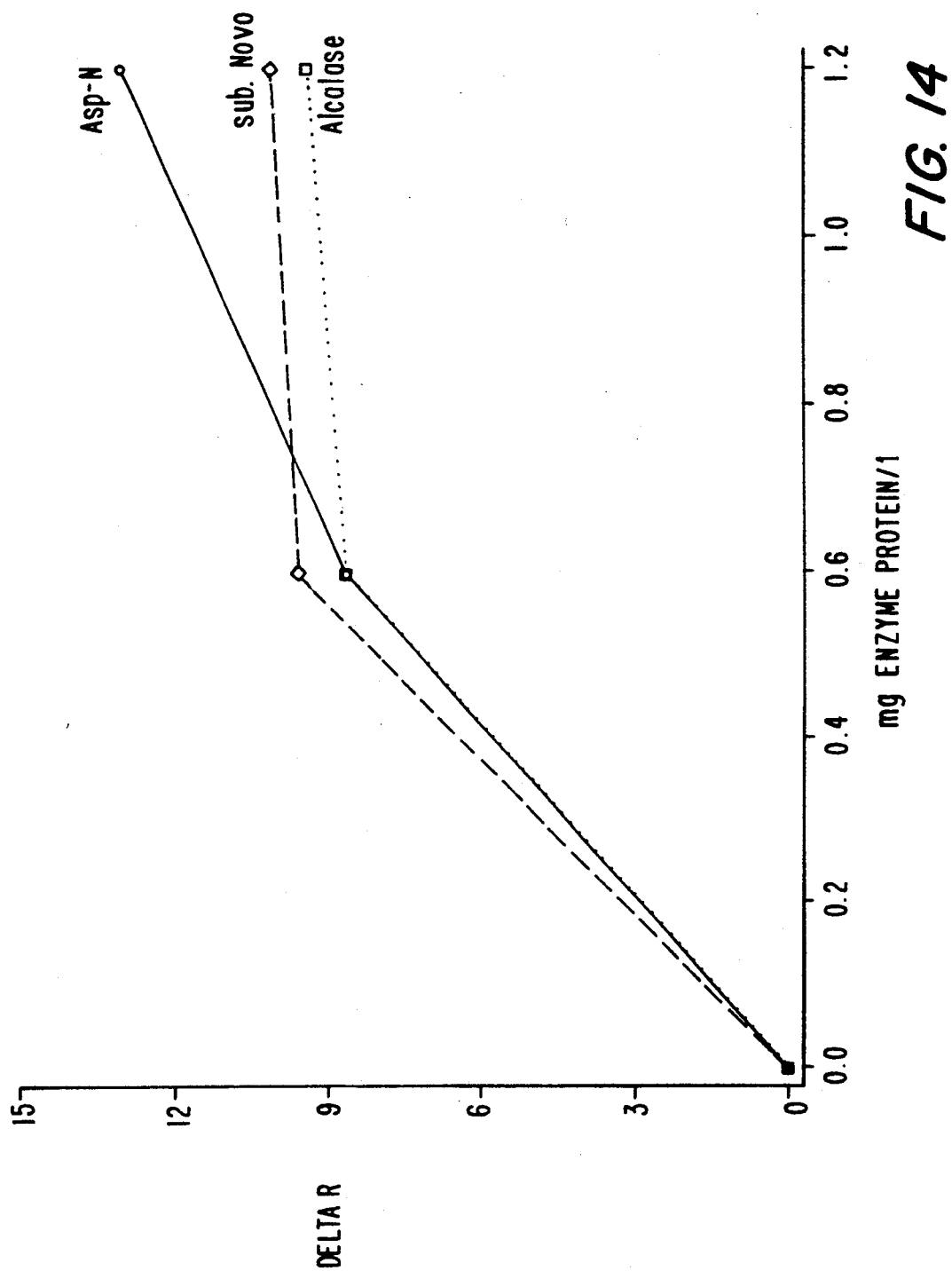
FIG. 14 shows the results of the washing tests in Example 10.

Results are given as delta R versus protease type and dosage in FIG. 14.

EXAMPLE 11

This example demonstrates how adsorption to cotton of hydrolysis products of hemoglobin varies with the type of protease used to hydrolyze the hemoglobin. It is shown that hydrolysis products formed by a specific protease (Trypsin) are adsorbed much less than those obtained with an unspecific protease (Subtilisin Carlsberg).

The method was as follows:

A 0.05% (w/v) solution of hemoglobin in Britton and Robinson I buffer, pH 9.0, was hydrolyzed by 0.3 CPU/l of a protease. After 30 minutes at 25° C. a cotton swatch (circular, 5 cm in diameter) was placed in the reaction mixture and it was boiled for 10 minutes. Then the swatch was removed, rinsed under running water, soaked in deionized water for 30 minutes and rinsed again under running water. After air-drying, reflectance (R) of the swatches at 460 nm was measured. The degree of adsorption is expressed as delta R=R—$R_o$, where $R_o$ is the reflectance obtained without enzyme, i.e. with unhydrolyzed hemoglobin.

The specific protease Trypsin and the unspecific protease Subtilisin Carlsberg were tested, separately and in combination. The results are shown in the following table:

| Total activity 0.3 CPU/1 | | |
|---|---|---|
| % Trypsin | % Carlsberg | Delta R |
| 0 | 100 | −6.8 |
| 100 | 0 | −0.1 |
| 90 | 10 | −3.8 |
| 50 | 50 | −5.0 |

A larger negative value of delta R indicates a darker swatch, i.e. more degradation products adsorbed.

The results show that the unspecific protease has a negative effect, i.e. leads to degradation products that are more easily adsorbed, whereas the specific protease has virtually no such effect. It is also seen that incorporation of even a minor proportion of the unspecific protease leads to significantly more adsorption results than with the pure specific protease.

We claim:

1. An endoprotease preparation, comprising an isolated endoprotease having the following characteristics:
   a) is a serine protease,
   b) shows immunochemical identity to a trypsin-like protease derived from *Fusarium oxysporum* DSM 2672 which hydrolyzes the oxidized beta-chain of bovine insulin at the peptide bonds Arg (22)-Gly (23) and Lys (29)-Ala(30),
   c) hydrolyzes the oxidized beta-chain of bovine insulin at the peptide bonds Arg (22)-Gly (23) and Lys (29)-Ala(30),
   d) has optimum activity towards casein in the pH range of 8.5–11 with nearly constant activity in said pH range,
   e) has optimum activity at a temperature of about 45° C., and
   f) has an isoelectric point of about 9–10, wherein the preparation is devoid of other proteases.

2. The endoprotease preparation according to claim 1, wherein the endoprotease is derived from *Fusarium oxysporum* DSM 2672.